United States Patent [19]

Kobayashi et al.

[11] Patent Number: 5,473,081
[45] Date of Patent: Dec. 5, 1995

[54] PROCESS FOR THE PREPARATION OF L-PROLINE DERIVATIVES

[75] Inventors: Yoshimasa Kobayashi; Kaori Tosa; Akihiro Sakimae; Ryozo Numazawa, all of Otake, Japan

[73] Assignee: Mitsubishi Rayon Co., Ltd., Tokyo, Japan

[21] Appl. No.: 181,168

[22] Filed: Jan. 13, 1994

Related U.S. Application Data

[63] Continuation of Ser. No. 847,304, Mar. 6, 1992, abandoned.

[30] Foreign Application Priority Data

Apr. 2, 1991 [JP] Japan .................................. 3-069916

[51] Int. Cl.$^6$ .................................................. C07D 207/12
[52] U.S. Cl. ............................................................ 548/533
[58] Field of Search ............................................ 548/533

[56] References Cited

PUBLICATIONS

Chemical Abstracts, vol. 95, No. 21, 181197z, Nov. 23, 1981, "Proline Derivatives as Antihypertensives".
Chemical Abstracts, vol. 106, No. 3, 19061z, Jan. 19, 1987, I. Linan Castellet, "1–(3–Mercapto–2–D–Methylpropanoyl)–L–Proline".
Chemical Abstracts, vol. 95, No. 7, 62706e, Aug. 17, 1981, "N–(D–(–Methyl–β–Mercaptopropionyl)–L–Proline Derivatives".
Chemical Abstracts, vol. 109, No. 3, 23391m, Jul. 18, 1988, J. M. Torres Esteban, et al., "Process for the Preparation of 3–Mercapto–2(S)–Methylpropionyl–L–Proline (Captopril)".
Chemical Abstracts, vol. 113, No. 17, 153042s, Oct. 22, 1991, J. M. Moniot, "Preparation of N–[2–(Mercaptomethyl)Propionyl ]–L–Proline".
Chemical Abstracts, 116, No. 3, 21464h, Jan. 20, 1992, X. Qi, et al., "Improved Synthesis of Captopril", Jun. 5, 1991.

*Primary Examiner*—Jacqueline Haley
*Attorney, Agent, or Firm*—Oblon, Spivak, McClelland, Maier, & Neustadt

[57] ABSTRACT

An L-proline derivative represented by:

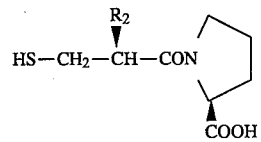

wherein $R_2$ represents a lower alkyl group is prepared by reacting L-proline with a D-α-alkyl-β-acylthiopropionic acid halide,

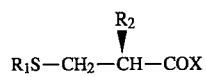

wherein $R_1$ represents an acyl group, X represents a halogen atom and $R_2$ has the same meaning as defined above. The halide is added to an aqueous medium containing L-proline and a condensation agent for deacidification. The halide and L-proline are reacted while the reaction temperature and pH are maintained at 12° C. or lower and within a range of 10.5–11.5, whereby a compound represented by:

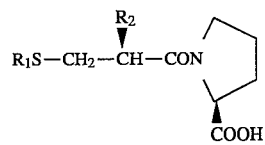

wherein $R_1$ and $R_2$ have the same meanings as defined above is obtained. The resulting compound is then subjected to deacylation under strong alkaline conditions without being isolated from the reaction mixture, thereby yielding the target L-proline derivative.

6 Claims, No Drawings

PROCESS FOR THE PREPARATION OF L-PROLINE DERIVATIVES

This application is a continuation of application Ser. No. 07/847,304, filed on Mar. 6, 1992, now abandoned.

BACKGROUND OF THE INVENTION

1. Field of the Invention

The present invention relates to a process for the preparation of optically-active N-(D-α-alkyl-β-mercaptopropionyl)-L-prolines.

2. Description of the Related Art

N-(D-α-methyl-β-mercaptopropionyl)-L-proline (common name: Captopril) represented by the following formula (IV):

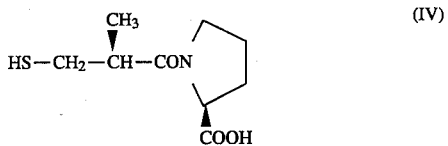

have been found extremely useful as hypotensive agents because of their strong inhibitory effect against the angiotensin-converting enzyme and marked hypotensive effect based on this enzyme inhibition (Biochemistry, 16, 5487 (1977)).

As a process for preparing such N-(D-α-alkyl-β-mercaptopropionyl)-L-prolines, it has been known to react optically-active D-α-alkyl-β-acylthiopropionic acid halides as starting materials with L-proline in an organic solvent or an aqueous medium, to isolate resulting N-(D-α-alkyl-β-acylthiopropionyl)-L-prolines and then to subject the thus-isolated compounds to deacylation, thereby yielding the N-(D-α-alkyl-β-mercaptopropionyl)-L-prolines as desired. Reactions in an organic solvent have been reported in Japanese Patent Laid-open No. 40676/1980, while those in an aqueous medium in Japanese Patent Laid-open No. 18985/1981.

The acid halides, starting materials, however, are unstable to water. Unless some special care is exercised for the reactions (amidation) between the acid halides and L-proline as in the present invention, hydrolysis of the acid halides occurs, resulting in the byproduction of D-α-alkyl-β-acylthiopropionic acids, which are hydrolysates of the acid halides. Therefore, organic solvents inert to the acid halides, such as halogenated hydrocarbons and tetrahydrofuran, are ordinarily used as reaction media for the amidation. Although the use of such organic solvents can prevent the hydrolysis of the acid halides, there is the problem that L-proline is only sparingly soluble in such organic solvents. It has, therefore, been inevitable to conduct the amidation by suspending L-proline in a solid form at the sacrifice of the reaction efficiency or to follow the cumbersome process that the reactions are conducted after converting L-proline to an ester soluble in such organic solvents.

In the above amidation, a condensation agent for deacidification is required for the scavenging of the hydrogen halide given off from the acid halides. The use of an organic solvent as a reaction medium, however, does not allow to employ an economical alkali metal hydroxide such as sodium hydroxide. It has, therefore, been inevitable to employ an expensive organic amine such as N,N-dimethylaniline from the viewpoint of its solubility in an organic solvent. Such an organic amine should be separated and recovered from the amides, the reaction products. The separation and recovery of the organic amine are, however, more difficult than those of the alkali metal hydroxide, leading to the problem that the unrecovered organic amine tends to mix in the products as an impurity.

Schotten-Baumann reactions between the acid halides and L-proline, when conducted in an aqueous medium, are not accompanied by such a problem as encountered in the reactions in an organic solvent, but hydrolysis of the acid halides arises as a new problem. In the process specifically described in Japanese Patent Laid-open No. 18958/1981, the acid halides are dissolved in an organic solvent such as tetrahydrofuran and the resulting solutions are added to an aqueous solution of L-proline to avoid the hydrolysis.

Such processes, however, use an organic solvent, thereby involving the problem of the need for complex post-treatment to separate and remove the organic solvent from the aqueous solutions of the resultant reaction products. In addition, various byproducts such as hydrolysates of the acid halide and reaction products produced by further reaction of Schotten-Baumann reaction products generally tend to occur in Schotten-Baumann reactions. If a Schotten-Baumann reaction product having an acyl group is subjected to deacylation in order to obtain a final product having a mercapto group as in the present invention, the purification of the final product will be difficult unless such byproducts are removed beforehand, because the final product is water-soluble. There has, hence, been no way other than following the steps that the Schotten-Baumann reaction product is once isolated and purified and then subjected to deacylation and the thus-obtained deacylation product is purified.

SUMMARY OF THE INVENTION

An object of the present invention is to provide a simple process for the preparation of an L-proline derivative in a high yield by, upon conducting the Schotten-Baumann reaction of an acid halide and L-proline in an aqueous medium, inhibiting the hydrolysis of the acid halide, thereby conducting deacylation without the need for isolation of the Schotten-Baumann reaction product from the reaction mixture.

With the foregoing circumstances in view, the present inventors have proceeded with extensive research on reaction parameters which may affect the production yield of the amidation product by the Schotten-Baumann reaction between an acid halide and L-proline and also the byproduction of the D-α-alkyl-β-acylthiopropionic acid and N-acyl-L-proline. As a result, it has been found that control of pH of the reaction mixture at a predetermined level with a condensation agent for deacidification makes it possible without the need for an organic solvent to prevent the hydrolysis of the acid halide and also to allow the amidation to proceed promptly and, in addition, to significantly inhibit the production of byproducts, such as N-acyl-L-proline, which are apt to occur at excessively high pH levels, whereby an amidation product can be obtained in a high yield. It has also been found that the amidation product obtained in the above manner can be subjected directly to deacylation without the need for its separation and purification from the reaction mixture in advance and, hence, an N-(D-α-alkyl-β-mercaptopropionyl)-L-proline can be obtained at a high purity and in a high yield, leading to the completion of the invention.

The present invention, therefore, provides a process for the preparation of an L-proline derivative represented by the formula (III):

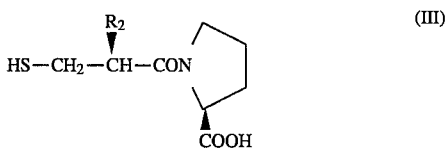

wherein $R_2$ represents a lower alkyl group by reacting a D-α-alkyl-β-acylthiopropionic acid halide, which is represented by the formula (I):

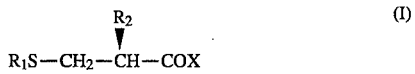

wherein $R_1$ represents an acyl group, X represents a halogen atom and $R_2$ has the same meaning as defined above, with L-proline. The process comprises adding the D-α-alkyl-β-acylthiopropionic acid halide (I) to an aqueous medium containing L-proline and a condensation agent for deacidification to react the D-α-alkyl-β-acylthiopropionic acid halide with L-proline while maintaining the reaction temperature below 12° C. and the pH within a range of 10.5–11.5, thereby yielding a compound represented by the formula (II):

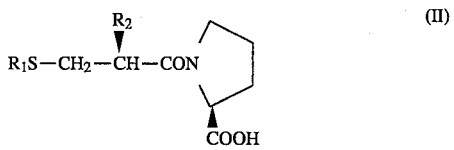

wherein $R_1$ and $R_2$ have the same meanings as defined above, and then subjecting the compound (II) to deacylation under strong alkaline conditions without isolating the same from the reaction mixture.

According to the process of the present invention, the byproduction of the D-α-alkyl-β-acylthiopropionic acid and N-acyl-L-proline can be suppressed in the amidation, whereby the N-(D-α-alkyl-β-acylthiopropionyl)-L-proline can be obtained at a high purity and in a high yield. Furthermore, by subjecting the above product to deacylation as it is according to the process of the present invention, the byproduction of D-α-alkyl-β-mercaptopropionic acid and N-acyl-L-proline can be suppressed, whereby the N-(D-α-alkyl-β -mercaptopropionyl)-L-proline can be obtained at a high purity and in a high yield.

DETAILED DESCRIPTION OF THE PREFERRED EMBODIMENTS

In the formulas (I) and (II), examples of the acyl group represented by $R_1$ include $C_{2-7}$ alkanoyl groups such as acetyl and propionyl groups; and aroyl groups such as benzoyl groups unsubstituted or substituted by one or more lower alkyl groups such as methyl, ethyl, n-propyl, i-propyl, n-butyl and t-butyl, or halogen atoms (fluorine, chlorine, bromine or iodine atoms). In the formulas (I), (II) and (III), examples of the lower alkyl group represented by $R_2$ include linear or branched $C_{1-7}$ alkyl groups such as methyl, ethyl, propyl and iso-propyl groups. In the formula (I), examples of the halogen atom represented by X include chlorine, bromine and iodine atoms.

The acid halide (I) useful in the practice of the present invention can be obtained, for example, by treating the corresponding carboxylic acid, which has been obtained by the process disclosed in Japanese Patent Laid-open No. 222798/1989, with a halogenating agent such as thionyl chloride, phosphorus trichloride or phosphorus tribromide by a method known per se in the art.

As the aqueous medium useful in the practice of the present invention, an aqueous solution having a pH of 10.5–11.5 may be employed.

Preferred examples of the condensation agent for deacidification include alkali compounds soluble in an aqueous medium, e.g., hydroxides of alkali metals such as sodium hydroxide and potassium hydroxide. The condensation agent for deacidification also serves as a pH controller for the aqueous medium.

In the practice of the present invention, the reaction between the acid halide and L-proline is conducted by adding the acid halide to an L-proline-containing aqueous medium, preferably under stirring. Upon reaction, the pH of the reaction mixture is maintained within a range of 10.5-11.5. An alkali metal hydroxide, which serves as a condensation agent for deacidification, is employed for scavenging the hydrogen halogenide given off from the acid halide and also for controlling the pH of the reaction mixture. Addition of an aqueous solution of L-proline to the acid halide is not preferred, because the residence time of the acid halide in the aqueous solution becomes so long that the hydrolysis of the acid halide occurs.

As the pH of the reaction mixture becomes lower than 10.5, that is, approaches toward the acidic side, the acid halide becomes more susceptible to hydrolysis. The closer the pH approaches toward pH 7, the more D-α -alkyl-β-acylthiopropionic acid, that is, the hydrolysate, is byproduced. PH lower than 10.5 is therefore not preferred. On the other hand, as the pH of the reaction mixture rises beyond 11.5 and approaches 14, more N-acyl-L-proline is byproduced. Accordingly, pH higher than 11.5 is not preferred either. Greater byproduction of N-acyl-L-proline at higher pH is probably attributed to the reaction of once-produced N-(D-α-alkyl-β-acylthiopropionyl)-L-proline with L-proline contained in the reaction mixture.

It is necessary to conduct the amidation below 12° C., preferably 10° C. or lower and more preferably 8° C. or lower. Temperatures higher than 12° C. result in the byproduction of N-acyl-L-proline in a larger amount as, therefore, are not preferred. Incidentally, it is preferable to conduct the reaction while maintaining the reaction mixture at 0° C. or higher in order to avoid undesirable freezing of the reaction mixture.

Although no particular limitation is imposed on the reaction time, the reaction time is preferably 0.5– 8 hours with 1–5 hours being more preferred.

It is economically advantageous to charge L-proline in an amount of 0.9–1.1 moles per mole of the acid halide. No particular limitation is imposed on the concentration of the aqueous solution of L-proline to be charged, but, it is preferable to add it at a concentration of 1–50 wt. %, preferably 2–30 wt. %, from the viewpoint of control of the reaction temperature.

The N-(D-α-alkyl-β-acylthiopropionyl)-L-proline, which has been produced by the reaction between the acid halide and L-proline, can be subjected to deacylation after its isolation and purification in a manner known per se in the art. In the process of the present invention, however, the reaction mixture after the amidation contains byproducts in an extremely small amount so that the amidation product can be subjected to deacylation in the same reactor while the reaction mixture being maintained under alkaline conditions without the need for its isolation after substantial completion of amidation.

The expression "after substantial completion of amidation" as used herein means the state that the amount of at least one of the acid halide and L-proline charged has decreased to 5% or less based on its charge.

Although no particular limitation is imposed on the range of the reaction temperature for the deacylation insofar as the reaction is conducted under alkaline conditions, it is preferable to raise the reaction temperature beyond 15° C., preferably to 20° C. or higher for the shortening of the reaction time. It is particularly preferred to conduct the reaction at a temperature between 40° C. and 50° C. and a pH between 10.5 and 11.5. The deacylation proceeds even at lower temperatures provided that the reaction mixture is maintained under strongly alkaline conditions of pH 12 or higher. Such lower temperatures are, however, economically disadvantageous because a large amount of a mineral acid is required for the extractive isolation of L-proline derivatives from the reaction mixture after the deacylation. On the other hand, pHs lower than 10.5 lead to the problem that more byproducts occur. PHs outside the above range are, therefore, not preferred.

The reaction time necessary for the deacylation ranges, in general, from 10 minutes to 10 hours, with 0.5–4 hours being preferred. In addition, it is preferable to conduct the deacylation in an atmosphere, preferably under a stream, of an inert gas such as nitrogen gas, helium gas and argon gas.

After the completion of the reaction, the reaction mixture is made acidic by the addition of a mineral acid such as hydrochloric acid. Then, the resulting N-(D-α -alkyl-β-mercaptopropionyl)-L-proline is extracted with an organic solvent such as dichloromethane and ethyl acetate and is dried under reduced pressure or recrystallized, whereby the target product can be isolated and obtained.

The present invention will hereinafter be described in more detail by the following examples. It should however be borne in mind that this invention is not limited to or by the following examples.

EXAMPLE 1

To 90 ml of distilled water, 5.8 g of L-proline were added. The resulting solution was adjusted to pH 11 by the addition of a 2N aqueous solution of sodium hydroxide. The resulting aqueous solution was cooled down to 5° C. or lower over ice-water bath. While the temperature of the reaction mixture was maintained at 5° C. or lower, 9.0 g of D-α-methyl-β-acetylthiopropionic acid chloride were added dropwise over 1 hour. After completion of the dropwise addition, they were reacted for additional 2 hours. Upon initiation of the dropwise addition, their reaction proceeded and the pH began to drop. A 2N aqueous solution of sodium hydroxide was, therefore, added through a pH controller pump during the reaction so that the pH of the reaction mixture was always maintained at 11.

After substantially no D-α-methyl-β-acetylthiopropionic acid chloride was detected in the reaction mixture, the reaction mixture was heated to 50° C. over warm-water bath under a nitrogen gas stream. With the elevation of the temperature of the reaction mixture, its pH began to drop again. While the pH of the solution was maintained at 11 by the addition of a 5N aqueous solution of sodium hydroxide through the pH controller pump, deacylation was conducted for additional 2 hours. After completion of the deacylation, the molar yield of the reaction product in the reaction mixture was analyzed by high-performance liquid chromatography. The results are shown in Table 1.

Replacement of D-α-methyl-β-acetylthiopropionic acid chloride by D-α-methyl-β-benzoylthiopropionic acid chloride in the same molar amount also permitted similar successful amidation and deacylation, resulting in the production of the corresponding L-proline derivative at a high purity and in a high yield.

COMPARATIVE EXAMPLES 1–4

A reaction was conducted in a similar manner to Example 1 except that the pH at the time of the amidation was always maintained at 7.6 (Comparative Example 1 where the aqueous solution of sodium hydroxide was replaced by an aqueous solution of sodium bicarbonate), 10.0 (Comparative Example 2), 12.0 (Comparative Example 3) or at least 13 (Comparative Example 4).

The molar yield of the reaction product in each reaction mixture was analyzed by high-performance liquid chromatography. The results are also shown in Table 1.

TABLE 1

|  | Example 1 | Comparative Example | | | |
|---|---|---|---|---|---|
|  |  | 1 | 2 | 3 | 4 |
| pH of the reaction mixture | 11.0 | 7.6 | 10.0 | 12.0 | ≧13 |
| Product (%) |  |  |  |  |  |
| 1 | 95.1 | 38.7 | 79.8 | 85.1 | 40.4 |
| 2 | 3.3 | 61.3 | 20.2 | 3.7 | 22.2 |
| 3 | 1.6 | 0 | 0 | 11.2 | 37.4 |

In Table 1 and Tables 2 and 3 to be described later, Product 1, Product 2 and Product 3 mean N-(D-α -methyl-β-mercaptopropionyl)-L-proline, D-α-methyl-β -mercaptopropionic acid and N-acyl-L-proline, respectively.

EXAMPLES 2 & 3

A reaction was conducted in a similar manner to Example 1 except that the pH was changed to 10.5 (Example 2) or 11.5 (Example 3). The molar yield of the product in each reaction mixture was analyzed by high-performance liquid chromatography. The results are shown in Table 2.

TABLE 2

|  | Example 2 | Example 3 |
|---|---|---|
| pH of the reaction mixture | 10.5 | 11.5 |
| Product (%) |  |  |
| 1 | 90.0 | 92.0 |
| 2 | 9.8 | 2.0 |
| 3 | 0.2 | 6.0 |

As is envisaged from the results of Examples 1–3 and Comparative Examples 1–4, the high-purity N-(D-α -alkyl-β-mercaptopropionyl)-L-proline can be obtained in a high yield by conducting amidation while maintaining the pH of the reaction mixture within the range defined in the present invention and, then, subjecting the resulting reaction product, as it is, to deacylation under alkaline conditions.

EXAMPLE 4 AND COMPARATIVE EXAMPLES 5 & 6

A reaction was conducted in a similar manner to Example 1 except that the temperature at the time of the amidation was changed. The results are shown in Table 3.

TABLE 3

|  | Example 4 | Comparative Example 5 | 6 |
|---|---|---|---|
| Reaction temperature (°C.) | 10 | 15 | 20 |
| Product (%) | | | |
| 1 | 90.2 | 83.8 | 78.7 |
| 2 | 7.8 | 6.2 | 8.6 |
| 3 | 3.0 | 10.0 | 12.7 |

What is claimed is:

1. A process for the preparation of an L-proline derivative represented by the following formula (III):

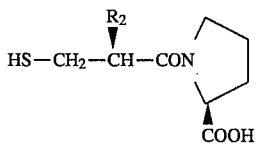

wherein $R_2$ represents a lower alkyl group by reacting a D-α-alkyl-β-acylthiopropionic acid halide, which is represented by the following formula (I):

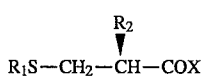

wherein $R_1$ represents an acyl group, X represents a halogen atom and $R_2$ has the same meaning as defined above, with L-proline, which comprises:

adding D-α-alkyl-β-acylthiopropionic acid halide (I) to an aqueous medium containing L-proline and an alkali metal hydroxide for deacidification while maintaining the reaction temperature at 12° C. or lower and pH within a range of 10.5 to 11.5, to obtain a compound represented by the following formula (II):

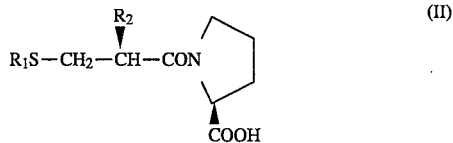

wherein $R_1$ and $R_2$ have the same meanings as defined above; and subjecting the compound (II) to deacylation without isolating the compound (II) from the reaction mixture by raising the temperature to at least 40° C. and maintaining the pH between 10.5 and 11.5 by adding an alkali metal hydroxide.

2. The process of claim 1, wherein the reaction between the D-α-alkyl-β-acylthiopropionic acid halide (I) and L-proline is conducted while maintaining the reaction temperature at 10° C. or lower.

3. The process of claim 1, wherein the alkali metal hydroxide is sodium hydroxide.

4. The process of claim 1, wherein the L-proline is used in an amount of 0.9 to 1.1 moles per mole of the D-α-alkyl-β-acylthiopropionic acid halide (I).

5. The process of claim 1, wherein the deacylation is conducted at 40° C. to 50° C. and pH 10.5 to pH 11.5.

6. The process of claim 1, wherein the L-proline derivative is N-(D-α-methyl-β-mercaptopropionyl)-L-proline represented by the following formula (IV):

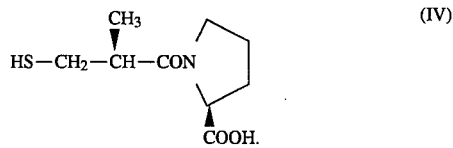

* * * * *